BLUEGRASS PLANT

Filed Jan. 7, 1971 2 Sheets-Sheet 1

United States Patent Office

Plant Pat. 3,239
Patented July 18, 1972

3,239
BLUEGRASS PLANT

Gerard William Pepin, North Brunswick, and Cyril Reed Funk, Jr., Milltown, N.J., assignors to E. F. Burlingham and Sons, Forest Grove, Oreg.

Filed Jan. 7, 1971, Ser. No. 104,819
Int. Cl. A01h *5/00*
U.S. Cl. Plt.—88 1 Claim

ABSTRACT OF THE DISCLOSURE

A Kentucky bluegrass plant which exhibits a very attractive, rich dark green color, rather prostrate leaf blades and rather large florets and spikelets. The plant produces a high quality turf with a good resistance to leaf spot and rust.

This invention relates to a new and distinct variety of bluegrass plant, the novel characteristics of which reside particularly in its very attractive, rich, dark green color which is maintained throughout the growing season, a rather prostrate leaf blade, good resistance to common turf diseases, particularly leaf spot and rust and its ability to produce a high quality turf.

The new variety was originated by us by crossing an unpatented selection identified in our breeding records as "Bellevue" with another unpatented selection identified as "Belturf," "Bellevue" being the seed parent and "Belturf" being the pollen parent. As a result of this breeding, we have produced and asexually propagated by rhizomes, tillers and disseminules a new and improved Kentucky bluegrass variety which is distinguished from its parents, as well as from all other varieties of which we are aware. The plants of the new variety were labeled "NJE P–84" Kentucky bluegrass.

NJE P–84 Kentucky bluegrass (*Poa pratensis* L.) is perennial with a leafy, rather prostrate, turf-type growth habit tolerant of moderately close mowing. The plant produces a very attractive, high quality turf with a rich dark green color and has good resistance to common turf diseases including leaf rust, stem rust, leaf spot and stripe smut.

In comparison with its seed parent, Bellevue, the new variety has finer leaves, a darker green color, maintains a more leafy turf during late spring, has better spreading ability, more prostrate leaf blades and better turf performance ratings.

In comparison with its pollen parent, Belturf, the new variety has shorter culms, more panicles per plant, better resistance to *Helminthosporium vagans,* more prostrate leaf blades and higher turf performance ratings.

In comparison with its sister selection, NJE P–69, the new variety has more prostrate leaf blades, shorter culms, larger seed and produces less pollen.

A primary object of this invention is to provide a new and distinct variety of Kentucky bluegrass plant having the desirable characteristics referred to above and to be described in detail below.

Other objects and advantages of the invention will become more apparent from the following detailed description when taken in conjunction with the accompanying illustrations, in which.

Figure 1:
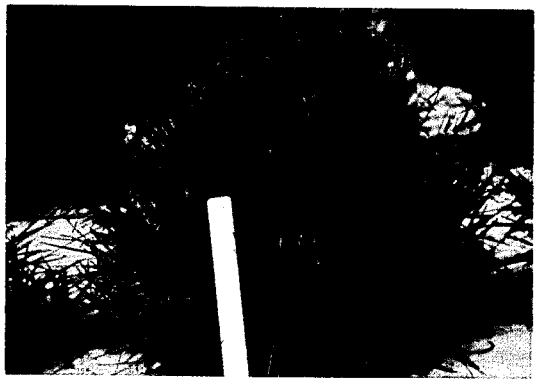
FIG. 1 shows a plant of the new variety approximately one week before the initiation of anthesis.
Figure 2:
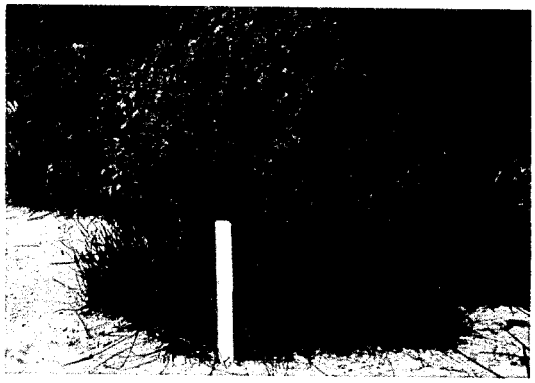
FIG. 2 shows a plant of the new variety under different lighting conditions at the time anthesis is nearing completion.
Figure 3:
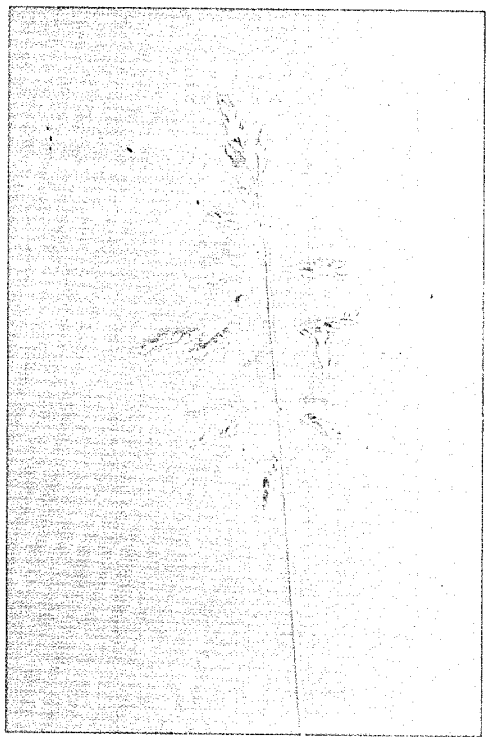
FIG. 3 shows a panicle of the new variety.
Figure 4:
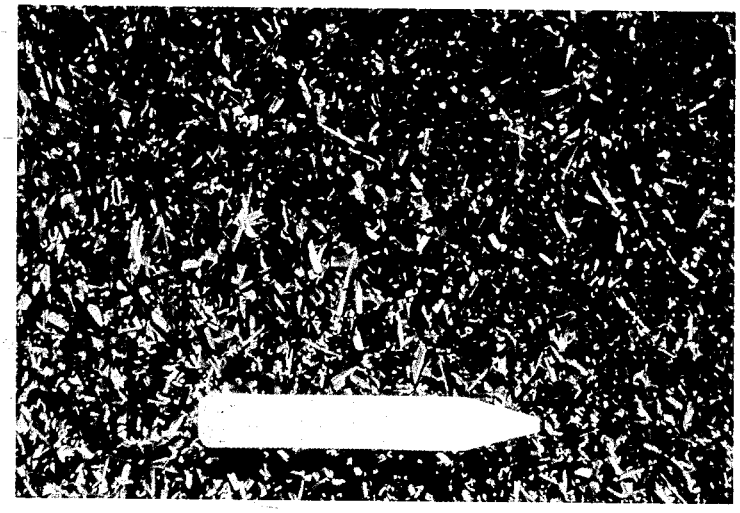
FIG. 4 shows a typical turf plot of the new variety.

NJE P–84 possesses at least the following unique combination of characteristics:

(1) Good resistance to the leaf spot and crown rot disease caused by the fungus *Helminthosporium vagans*;

(2) Moderately good resistance to the stripe smut disease caused by the fungus *Ustilago striiformis*;

(3) Good resistance to the leaf rust disease caused by the fungus *Puccinia poae-nemoralis*;

(4) Good resistance to the stem rust disease caused by the fungus *Puccinia graminis*;

(5) A very attractive, rich dark green color which is maintained throughout the entire growing season;

(6) Leaf blades of medium width;

(7) Moderately prostrate leaf blades;

(8) Rather large spikelets, florets and seed;

(9) Low pollen production;

(10) Good rhizome and tiller development under turf maintenance producing a strong turf of excellent density and good horizontal spreading ability;

(11) A leafy turf-type growth habit which can tolerate fairly close mowing;

(12) Very good turf performance.

PLANT DESCRIPTION

The plants of the new variety which are described herein were grown in New Jersey. Spikelet measurements are based on Oregon grown plants. The culms of the variety are usually bent at lowest nodes becoming generally erect, tufted and averaged 64 cm. in height when undisturbed by clipping, are moderately stout, cylindrical, usually with four nodes, and smooth. Leaves are dark green with blades 3 to 4 mm. wide (average 3.7 mm.), initially folded and subsequently opening out with a boat shaped apex. Ligules are membranous, finely pubescent and very short on vegetative tillers but average 1.6 mm. long on the flag leaf. Panicles are pyramidal and open, with main axis moderately erect averaging 109 mm. long with lower branches in clusters of 3 to 5 (average 3.9). Spikelets are ovate, compressed, 5 to 7 mm. long (average 6.0 mm.), 5 to 6 flowered (average 5.3), breaking up at maturity beneath each lemma. Glumes persistent, pointed, rough on the keels; lower ovate 3.0 to 3.7 mm. long (average 3.3 mm.), 1 to 3 nerved; upper ovate to elliptic, 3.2 to 3.9 mm. long (average 3.5 mm.), three-nerved. Lemmas are overlapping, ovate-oblong in side view, slightly pointed, 3.0 to 3.6 mm. long (average 3.1 mm.), moderately hairy on the lower one-half to two-thirds of the keel and marginal nerves, with long fine crinkled hairs at the base, finely five-nerved. with thin tips and margins. Paleas not as long as the lemmas with two rough keels. Caryopsis enclosed by the hardened lemma and palea.

Since environmental factors such as daylength, temperature, soil fertility and moisture influence morphological characteristics to some degree these characters may vary slightly under different conditions. The morphological characteristics of NJE P–84 and other bluegrasses measured during 1970 at Adelphia, N.J., are shown in Table 1.

TABLE 1.—MORPHOLOGICAL COMPARISON OF NJE P-84 AND OTHER BLUEGRASS VARIETIES

| Variety | Plant height, cm. | Plant diameter cm. | Leaf blade width, mm. | Hairs on edge of collar [1] | Hairs on ligule [1] | Flag leaf length mm. | Number of panicles per plant | Panicle color [2] | Panicle erect or nodding [3] | Number of branches at lowest panicle node | Panicle length mm. |
|---|---|---|---|---|---|---|---|---|---|---|---|
| P-69 | 73 | 34 | 3.7 | 3.5 | 2.7 | 52 | 272 | 2.0 | 1.8 | 3.7 | 104 |
| P-84 | 64 | 39 | 3.7 | 2.0 | 2.0 | 63 | 223 | 2.0 | 2.5 | 3.9 | 109 |
| Delta | 73 | 17 | 2.6 | 1.5 | 0.0 | 67 | 196 | 2.0 | 1.0 | 4.8 | 100 |
| Geary | 80 | 24 | 2.9 | 2.0 | 0.0 | 80 | 177 | 3.0 | 3.0 | 4.0 | 134 |
| Newport | 79 | 30 | 4.8 | 3.7 | 3.7 | 77 | 246 | 2.5 | 2.0 | 4.3 | 105 |
| Palouse | 79 | 24 | 3.0 | 1.0 | 0.0 | 93 | 151 | 3.0 | 3.5 | 4.4 | 92 |
| Anheuser Dwarf | 67 | 30 | 5.1 | 2.5 | 2.0 | 51 | 109 | 3.0 | 2.5 | 3.4 | 96 |
| Belturf | 70 | 35 | 3.0 | 2.0 | 1.0 | 58 | 201 | 2.0 | 2.0 | 4.0 | 104 |
| Fylking (Patent 2887) | 60 | 34 | 4.0 | 1.5 | 1.5 | 68 | 164 | 3.5 | 5.0 | 4.9 | 118 |
| Merion | 70 | 24 | 4.3 | 3.5 | 0.5 | 69 | 280 | 2.0 | 1.5 | 3.5 | 102 |
| Pennstar | 59 | 34 | 3.7 | 2.2 | 1.0 | 66 | 132 | 3.5 | 4.0 | 4.5 | 106 |

[1] Scale: 0=no hairs; 5=most hairs. [2] Scale: 0=green; 5=purple. [3] Scale: 1=erect; 5=nodding.

CHARACTERISTICS OF CARYOPSIS

The characteristics of the caryopsis of NJE P-84 are shown in Table 2.

TABLE 2.—CARYOPSIS CHARACTERISTICS OF NJE P-84

| Character | Description |
|---|---|
| 1 Intermediate nerves on lemma. | Indistinct. |
| 2 Lemma color | Evenly brownish, some with darker base. |
| 3 Lemma margins and apex. | Apex flared out from sharp keel, wide hyline margins toward the top (may be frayed on commercially processed seed), tapers to medium point in side view; longer and markedly wider than palea. |
| 4 Lemma texture | Granular. |
| 5 In lateral plane—floret shape plus thickness or plumpness. | Mass of seed evenly distributed, lemma side straight or evenly arched. |
| 6 Length | 2.5 to 3.5 mm. (average 3.1 mm.). |
| 7 Width | 0.6 to 0.9 mm. (average 0.74 mm.). |

NJE P-84 has large seed, with one pound of Oregon produced seed containing 1,145,000 seeds. For comparison, Merion is reported to produce about 2,000,000 seeds per pound, Windsor about 1,521,000 seeds per pound, NJE P-69 about 1,350,000 seeds per pound and Common Kentucky bluegrass about 1,600,000 seeds per pound.

CYTOLOGICAL CHARACTERISTICS

Studies of pollen mother cell meiosis indicate NJE P-84 has about 82 chromosomes. Root tip paraffin sections of Bellevue, the female parent of NJE P-84, indicates about 56 chromosomes. Studies of pollen mother cell meiosis and studies of mitosis in the apical meristem both indicate that Belturf, the male parent of NJE P-84, has 49 chromosomes. NJE P-84 thus appears to be "triploid," combining all the chromosomes of Bellevue with about one-half the chromosomes of Belturf.

REPRODUCTION AND PROPAGATION

Asexual reproduction of NJE P-84 by propagules (tillers and rhizomes) and by disseminules (modified caryopses produced by agamospermy) has consistently produced progeny plants indistinguishable from the mother plant.

TURF PERFORMANCE

Overall turf performance ratings for NJE P-84 and other Kentucky bluegrasses for the years 1966 through 1970 at New Brunswick, N.J., are presented in Table 3.

TABLE 3.—TURF PERFORMANCE RATINGS OF NJE P-84 AND OTHER BLUEGRASSES IN TEST ESTABLISHED IN 1965

| Variety | Turf performance score, 10=best | | | | | |
|---|---|---|---|---|---|---|
| | 1966 | 1967 | 1968 | 1969 | 1970 | Avg. |
| NJE P-84 | 7.3 | 7.7 | 8.4 | 8.1 | 7.7 | [1] 7.8a |
| NJE P-69 | 6.8 | 7.3 | 8.2 | 7.3 | 6.9 | 7.3a |
| Anheuser Dwarf | 7.6 | 7.3 | 7.5 | 6.9 | 7.6 | 7.4a |
| Fylking | 6.9 | 6.8 | 8.0 | 7.6 | 7.2 | 7.3a |
| Pennstar | 6.9 | 6.8 | 7.9 | 7.1 | 7.2 | 7.2ab |
| Belturf | 6.2 | 5.9 | 7.4 | 7.0 | 6.2 | 6.5b |
| Bellevue | 6.4 | 6.7 | 6.9 | 5.9 | 5.7 | 6.3bc |
| Merion | 6.3 | 6.1 | 6.8 | 4.9 | 4.1 | 5.6cd |
| Windsor | 5.0 | 5.0 | 6.4 | 5.4 | 4.3 | 5.2de |
| Delta | 4.5 | 4.2 | 5.2 | 4.9 | 4.5 | 4.7e |

[1] Values within a column followed by the same letter do not differ significantly at the five percent probability level.

The new variety has demonstrated consistently high turf performance. Of particular importance is its very attractive, rich dark green color which lasts from early spring throughout the entire growing season. Observation of the new variety and similar varieties during ho,t dry periods in the summer months has shown that the dark green color is not merely an early spring characteristic. The variety also exhibits high quality ratings, good turf density and adequate sod strength as shown in Tables 4 and 5.

TABLE 4.—TURF PERFORMANCE AND SPRING COLOR RATINGS OF NJE P-84 AND OTHER KENTUCKY BLUEGRASS VARIETIES IN TEST ESTABLISHED IN 1967

| Variety | Turf quality, 9=best | | Spring color 9=most attractive March 1970 |
|---|---|---|---|
| | 1969 | 1970 | |
| NJE P-84 | 7.5 | 7.7 | 6.0 |
| NJE P-69 | 7.4 | 7.5 | 6.0 |
| Anheuser Dwarf | 7.6 | 7.0 | 2.4 |
| Pennstar | 7.5 | 6.8 | 3.0 |
| Fylking | 7.3 | 6.8 | 3.0 |
| Merion | 6.3 | 6.0 | 3.0 |
| Belturf | 6.1 | 4.9 | 3.0 |
| Windsor | 5.0 | 5.1 | 3.0 |
| Primo | 4.8 | 4.0 | 1.0 |
| Delta | 3.9 | 3.0 | 4.0 |
| Delft | 3.4 | 3.3 | 6.0 |
| Park | 2.9 | 2.3 | 2.5 |
| Kenblue | 2.8 | 2.1 | 3.0 |
| South Dakota Common | 2.3 | 1.6 | 2.0 |
| Troy | 1.7 | 1.1 | 3.0 |
| LSD at 5 percent | 1.1 | 1.0 | 1.2 |

TABLE 5.—TURF PERFORMANCE, SPRING COLOR AND DENSITY RATINGS OF NJE P-84 AND OTHER KENTUCKY BLUEGRASS VARIETIES IN TEST ESTABLISHED IN 1968

| Variety | Turf quality, 9=best | | Spring color, 9=most attractive, March 1970 | Turf density, 9=most dense, 1970 | Sod strength, pounds per foot, August 1969 |
|---|---|---|---|---|---|
| | 1969 | 1970 | | | |
| NJE P-84 | 7.9 | 7.9 | 7.7 | 7.4 | 53 |
| Fylking | 7.3 | 7.2 | 3.9 | 6.9 | 67 |
| Pennstar | 7.2 | 7.0 | 3.7 | 7.4 | 58 |
| Sodco | 7.2 | 6.8 | 2.8 | 6.4 | 48 |
| Belturf | 6.8 | 7.1 | 4.0 | 7.7 | 50 |
| Merion | 6.6 | 6.9 | 3.9 | 7.2 | 36 |
| Windsor | 4.5 | 4.8 | 4.3 | 4.2 | 18 |
| Newport | 5.0 | 4.4 | 5.0 | 4.7 | 19 |
| Park | 4.7 | 3.9 | 5.9 | 3.8 | 27 |
| Kenblue | 4.1 | 3.3 | 5.9 | 2.2 | 27 |
| Delta | 2.9 | 2.5 | 4.4 | 2.2 | 22 |
| Common | 3.4 | 2.7 | 4.7 | 1.7 | 8 |
| LSD at 5 percent | 0.4 | 0.3 | 0.9 | 0.6 | |

DISEASE RESISTANCE

A comparison of NJE P–84 and other Kentucky bluegrasses for resistance to thel eaf spot and crown rot disease caused by the fungus *Helminthosporium vagans,* the stripe smut disease caused by the fungus *Ustilago striiformis,* and the leaf rust disease caused by the fungus *Puccinia poae-nemoralis* is presented in the following tables:

TABLE 6.—RELATIVE COMPARISON OF LEAF SPOT AND CROWN ROT DISEASE RESISTANCE FOR NJE P–84 AND OTHER KENTUCKY BLUEGRASSES AT NEW BRUNSWICK, N.J. IN 1970

| Variety | Percent disease damage | | |
|---|---|---|---|
| | Test 1, established in 1965 | Test 2, established in 1967 | Test 3, established in 1968 |
| NJE P–84 | 6a [1] | 6a | 4a |
| Merion | 5a | 5a | 5a |
| Pennstar | 6a | 6a | 5a |
| Fylking | 6a | 6a | 5a |
| Bellevue | 10b | 13b | |
| Belturf | 20c | 20c | 13b |
| Windsor | 28d | 25c | 47c |
| Delta | 70e | 80d | 81d |
| Park | | 85de | 84d |
| Kenblue | | 90ef | 89de |
| South Dakota Common | | 95f | 92e |

[1] Values within a column followed by the same letter do not differ significantly at the five percent probability level.

TABLE 7.—RELATIVE COMPARISON OF STRIPE SMUT DISEASE RESISTANCE FOR NJE P–84 AND OTHER KENTUCKY BLUEGRASSES AT NEW BRUNSWICK, N.J.

| Variety: | Stripe smut infected tillers per square foot |
|---|---|
| NJE P–84 | [1] 2a |
| Fylking | 0a |
| Pennstar | 0a |
| Anheuser Dwarf | 0a |
| Belturf | 2a |
| Bellevue | 11b |
| Delta | 11b |
| Windsor | 41c |
| Merion | 228d |

[1] Values followed by the same letter do not differ significantly at the five percent probability level.

TABLE 8.—RELATIVE COMPARISON OF LEAF RUST DIEASE LEVEL FOR NJE P–84 AND OTHER KENTUCKY BLUEGRASSES AT ADELPHIA, N.J., IN 1970

| Variety: | Rust disease rating [1] |
|---|---|
| NJE P–84 | [2] 1.5a |
| Pennstar | 1.5a |
| Fylking | 1.5a |
| Prato | 2.0ab |
| Geary | 3.0bc |
| Newport | 3.5c |
| Merion | 3.5c |
| NJE P–117 | 7.5d |

[1] Scale: 0=no rust; 9=most disease.
[2] Values within a column followed by the same letter do not differ significantly at the five percent probability level.

What is claimed is:

1. A new and distinct variety of Kentucky bluegrass plant, substantially as herein shown and described, characterized particularly by very good turf performance, a very attractive, rich, dark green color, rather horizontal leaf blades, good rhizome and tiller development, large florets and spikelets and good resistance to leaf spot and rust.

No references cited.

ROBERT E. BAGWILL, Primary Examiner